United States Patent [19]

Ransford et al.

[11] Patent Number: 5,324,874

[45] Date of Patent: Jun. 28, 1994

[54] PROCESS FOR A DECARBROMODIPHENYLETHANE PREDOMINATE PRODUCT HAVING ENHANCED WHITENESS

[75] Inventors: George H. Ransford; Phillip R. DeVrou, both of Magnolia, Ark.; John C. Parks, Baton Rouge, La.

[73] Assignee: Ethyl Corporation, Richmond, Va.

[21] Appl. No.: 930,809

[22] Filed: Aug. 17, 1992

Related U.S. Application Data

[63] Continuation-in-part of Ser. No. 887,909, May 26, 1992, abandoned.

[51] Int. Cl.$^5$ .................... C07C 17/12; C07C 25/18
[52] U.S. Cl. .................... 570/208; 570/184; 570/206; 570/210; 570/211
[58] Field of Search ............... 570/184, 206, 208, 210, 570/211

[56] References Cited

U.S. PATENT DOCUMENTS

| | | | |
|---|---|---|---|
| 2,033,612 | 3/1936 | Clark et al. | 260/161 |
| 2,244,284 | 6/1941 | Britton et al. | 260/649 |
| 3,141,860 | 7/1964 | Sauer et al. | 260/33.8 |
| 3,232,959 | 2/1966 | Hahn | 260/389 |
| 3,285,965 | 11/1966 | Jenkner | 260/612 |
| 3,331,797 | 7/1967 | Kopetz et al. | 260/28.5 |
| 3,763,248 | 10/1973 | Mitchell | 260/649 D |
| 3,833,674 | 9/1974 | Brackenridge | 260/649 DP |
| 3,959,387 | 5/1976 | Brackenridge | 260/612 R |
| 3,965,197 | 6/1976 | Stepniczka | 260/623 H |
| 4,287,373 | 9/1981 | Garman et al. | 568/639 |
| 4,521,633 | 6/1985 | Pedjac | 568/639 |
| 4,639,481 | 1/1987 | Giles, Jr. | 524/128 |
| 4,666,947 | 5/1987 | Brichta et al. | 521/79 |
| 4,740,629 | 4/1988 | Brackenridge et al. | 568/639 |
| 5,008,477 | 4/1991 | Hussain | 570/211 |
| 5,030,778 | 7/1991 | Ranford | 570/206 |

FOREIGN PATENT DOCUMENTS

| | | |
|---|---|---|
| 708209 | 4/1965 | Canada . |
| 0265150 | 4/1988 | European Pat. Off. . |
| 2950877 | 6/1981 | Fed. Rep. of Germany . |
| 39639 | 3/1977 | Japan . |
| 116332 | 10/1978 | Japan . |
| 116333 | 10/1978 | Japan . |
| 116334 | 10/1978 | Japan . |
| 70060 | 6/1981 | Japan . |
| 981833 | 1/1965 | United Kingdom . |
| 991067 | 5/1965 | United Kingdom . |
| 1411524 | 10/1975 | United Kingdom . |
| 1472383 | 5/1977 | United Kingdom . |

OTHER PUBLICATIONS

"Flammfestmachen von Kunststoffen" by Dr. Hans Vogel, p. 49.

By Green et al. in "Fire Retardants": Proceedings of 1974 International Symposium on Flammability and Fire Retardants, pp. 68–76, 1974.

By Inaba et al. in the 'Journal of Organic Chemistry', 49 (12), pp. 2093–2098, 1984.

By Corey et al. in the 'Journal of Organicmetallic Chemistry', 210 (2), pp. 149–161, 1981.

By Gassman et al. in the 'Journal of Organic Chemistry', 47 (20), pp. 4002–4004, 1982.

CAS Registry Handbook-Reg. No. 84852-53-9.

*Primary Examiner*—Paul R. Michl
*Assistant Examiner*—Tae H. Yoon
*Attorney, Agent, or Firm*—David E. LaRose

[57] ABSTRACT

This invention relates to an improvement in a process for preparing a product predominant in decabromodiphenylethane. In the improved process the diphenylethane is reacted with bromine in the presence of bromination catalyst in a reaction vessel by feeding diphenylethane to the reaction vessel below the liquid level of bromine in the reaction vessel. The improvement comprises contacting diphenylethane, bromine, and catalyst at a rate sufficient to obtain a diphenylethane predominant product having enhanced color and particle size.

6 Claims, 1 Drawing Sheet

TEMPERATURE VERSUS TIME

PROCESS FOR A DECARBROMODIPHENYLETHANE PREDOMINATE PRODUCT HAVING ENHANCED WHITENESS

BACKGROUND OF THE INVENTION

This application is a continuation-in-part of patent application Ser. No. 887,909, filed MAY 26, 1992 abandoned.

This invention relates to a process for preparing a product which is predominate in decabromodiphenylethane and which has a Yellowness Index, as determined by ASTM D 1925, which is less than about 11.

Decabromodiphenylethane is known as a flame retardant for use in polyolefin, and in polystyrene based formulations, however, at present, it is not considered to be commercially significant. Due to the fact that this flame retardant is not associated with the production of dioxin and other non-desirable compounds under thermoplastic blending or molding conditions, it is expected that it will obtain a greater market presence. When sold in commercial quantities, this flame retardant will most probably not be provided in the pure form, but rather it will be provided as the principal constituent of a product which will additionally contain small amounts of impurities. Generally, such products will contain at least about 90 wt % decabromodiphenylethane, with the balance being the impurities. While such products have been demonstrated to be useful in many applications, they may be limited in use due to their less than white color. Indeed, some decabromodiphenylethane predominate products are distinctly tan or have a readily seen reddish hue. It is believed that these color characteristics may be due, at least in part, to the morphology of the decabromodiphenylethane and/or to the presence in the product of chromophoric impurities. Generally, the particular chromophoric impurities seen and their amounts and the obtained morphology are due to the peculiar characteristics of the process used in producing the product and due to the particular impurities found in the reactants.

The motivation to obtain as white a product as is possible is not based upon a search for an improvement in flame retardency, but rather, is based upon the needs of the molding industry. The molding industry produces thermoplastic articles of all colors, some light and some dark. The lighter colors, which include white, cannot easily be produced from thermoplastic formulations which contain colored constituents, e.g. colored decabromodiphenylethane. It would be ideal, from a color standpoint, if all the formulation constituents were pure white except for those dyes etc. specifically added to obtain a desired color. The existence of a pure white decabromodiphenylethane product, i.e. one having a Yellowness Index ASTM 1925 (hereinafter Y.I.) of 0.0, is not presently known. While products having a Y.I. within the range of from 15 to about 11 have been made, such products are not the ideal. The obtainment of a Y.I. value in the range of 5 to below 11 would represent a significant step. Indeed, Y.I. values of about 6–7 are, to the human eye, very near to the ideal of pure white.

SUMMARY OF THE INVENTION

Accordingly, this invention provides an improvement in a process for preparing a product predominant in decabromodiphenylethane, wherein the diphenylethane is reacted with bromine in the presence of bromination catalyst in a reaction vessel by feeding diphenylethane to the reaction vessel below the liquid level of bromine in the reaction vessel. The improvement comprises contacting diphenylethane, bromine, and catalyst at a rate sufficient to obtain a diphenylethane predominant product having enhanced color and particle size. By enhanced color is meant having a Y.I. of less than about 11. A preferred product is one having a Y.I. which is within the range of from about 5 to about 8.5, and most preferably within the range of from about 5 to about 7.

In another embodiment, this invention provides a process for preparing a product predominant in decabromo-1,2-diphenylethane by reacting 1,2-diphenylethane with bromine in the presence of a catalytic amount of bromination catalyst in a reaction vessel. The process comprises (a) feeding an amount of diphenylalkane to the reaction vessel, below the liquid level of bromine in the reaction vessel, at a rate in the range of from about 50 to about 600 centimeters per second; (b) maintaining said 1,2-diphenylethane, bromine, and catalyst at a temperature in the range of from about 30° to about 80° C. during said feeding and reaction and (c) recovering said product predominant in decabromo-1,2-diphenylethane which product has an average particle size of greater than about 15 microns.

In yet another embodiment, this invention provides a process for preparing a product predominant in decabromodiphenylethane having a yellowness index (Y.I.) value of between about 5 to about 11 as measured by ASTM D 1925, and a particle size of greater than about 15 microns. The process comprises (a) feeding an amount of diphenylethane to a reaction vessel containing bromine and a bromination catalyst; (b) maintaining, during the feeding, a reaction time-temperature profile whereby the rate of reaction between the diphenylethane and bromine is maximized so as to minimize color causing side reactions; (c) separating the decabromodiphenylethane predominant product from the bromine and catalyst; and (d) heat treating the product at a temperature and for a period of time sufficient to obtain a product having a yellowness index (Y.I.) value between about 5 and about 11 as measured by ASTM D 1925.

Other embodiments of the invention will be evident from the ensuing description and claims.

DETAILED DESCRIPTION

Figure 1:
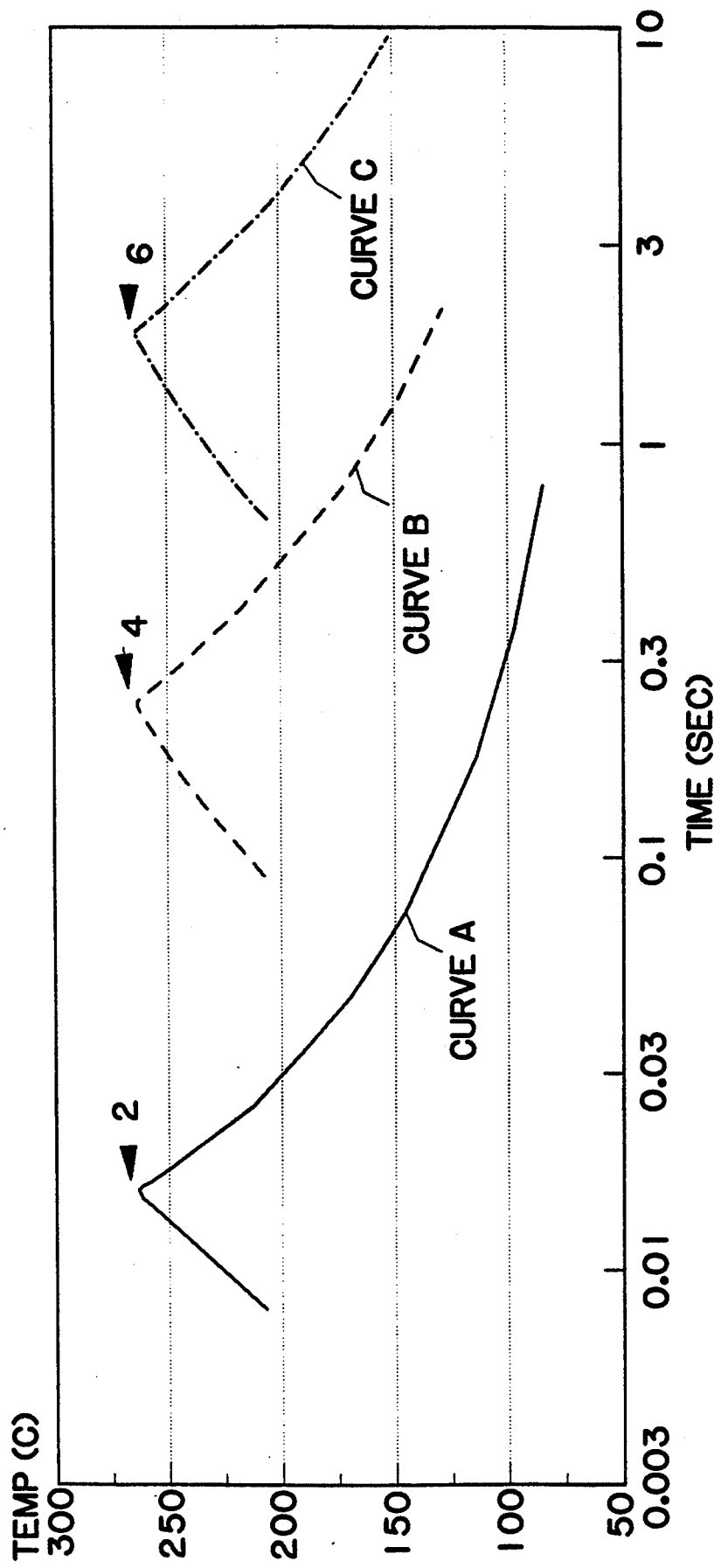
FIG. 1 illustrates a theoretical perbromination temperature-time relationship for several diphenylethane feed rates.

Until now, the preparation of decabromodiphenylethane products having good color characteristics and large particle size has been difficult to achieve. The processes which are useful in preparing good color decabromodiphenyl oxide having large size particles, must be modified dramatically in order to achieve decabromodiphenylethane products with enhanced color characteristics and large particle size. It is believed that these difficulties arise in part due to color causing side reactions which occur much more rapidly when brominating diphenylethane as compared to diphenyl oxide bromination. Based, at least in part, on this belief, it has been discovered that increasing the rate with which each molecule of diphenylethane reacts with 10 moles of bromine, can provide products having improved size and color characteristics. Thus, on a microscopic basis, each mole of diphenylethane in a droplet of diphenylethane should be admixed with at least about 10 moles of bromine in the shortest time possible. This so called "micro-mixing" of diphenylethane and bromine is therefore a key feature of this invention. Suitable micro-mixing can be achieved in a number of ways such as by increasing the agitation rate during the diphenylethane feeding or by decreasing the dip tube size while increasing the diphenylethane feed rate. On a commercial scale, it is easier, and less costly to increase the diphenylethane feed rate rather than to increase the agitation rate. Regardless of the actual means chosen to achieve the enhanced product of this invention, this invention contemplates variations within its spirit and scope which reduce the amount of color causing impurities in the decabromodiphenylethane predominant products thus produced.

By stating that the product of this invention is predominate in decabromodiphenylethane it is meant that the product contains impurities and at least about 90 wt % decabromodiphenylethane. The preferred products of this invention contain from about 95 to about 99.5 wt % decabromodiphenylethane. The most preferred products contain from about 98 to about 99.5 wt % decabromodiphenylethane.

The impurities in the products of this invention can include one or more of: bromine; nonabromodiphenylethane; aluminum salts; sodium bromide; water; dodecabromodiphenylethane; brominated olefins, e.g. brominated stilbene; brominated diphenylmethane; polybrominated benzene; and brominated alkylbenzenes. The bromine is usually the most predominate impurity from a quantitative view. Depending on the amount of free bromine present in the crude dry product, the dodecabromodiphenylethane content can range from 0 to 10,000 ppm. The other impurities are generally present in amounts of from 0 to 500 ppm. Morphologically, the decabromodiphenylethane constituent of the product of this invention is believed to have some crystallinity —the major morphological quality being amorphic.

As is well recognized in the flame retardant art, ar-brominated flame retardants, e.g. octabromodiphenyl oxide, decabromodiphenyl oxide, decabromodiphenylethane and the like, are really mixtures of various bromo-homologs with one or two bromo-homologs comprising the greatest percentage of all bromo-homologs present. To simplify the naming of these mixtures, the art has adopted the system of naming such a mixture according to the bromo-homolog name which is proper for that homolog which represents the average number of ar-substituent bromine atoms per molecule. If the average is a mixed number, then the average is simply rounded up to the next whole number. For example, if the ar-bromine average of a polybromodiphenyl oxide mixture is 7.3 or 8.0, then the mixture is referred to as octabromodiphenyl oxide. Hence, the term, decabromodiphenylethane, when used in conjunction with the description of a product of this invention, denotes a mixture of polybromodiphenylethanes having an average of between 9+ and 10 ar-bromines per molecule of polybromodiphenylethane in the mixture.

Typically, the distribution for the bromo-homolog mixture making up the decabromodiphenylethane portion of the product of this invention will include about 0–1.5% octabromodiphenylethane, about 0–8% nonabromodiphenylethane, and the balance being decabromodiphenylethane. Preferred bromo-homolog distributions are about 1–2% nonabromodiphenylethane, and about 98–99% decabromodiphenylethane. The most preferred bromo-homolog distributions contain at least about 95% decabromodiphenylethane. The foregoing percentages are gas chromatography area percentages.

The melting point, hereafter m.p., of the decabromodiphenylethane predominate product of this invention does not occur at a single point but rather over a range of temperatures. The m.p. range has a lower value at which melting is first noticed and an upper value at which the last of the product is seen to melt. The lower values are typically from about 344° C. to about 346° C. while the upper values are from about 346° C. to about 354° C. The products of this invention exhibit rather narrow m.p.'s. Preferred products, exhibit a m.p. of about 346°–350° C., while most preferred products will exhibit a m.p. of about 348°–354° C.

In the flame retardant industry it is considered beneficial to provide a product which has a low free halogen content. The products of this invention exhibit such a content. Typically, they will contain no more than about 500 ppm free bromine. Preferably the free bromine content will not exceed 100 ppm, and most preferably less than about 50 ppm free bromine. The term, free bromine, is meant to define bromine which is present in the product in the form of $Br_2$.

Good thermal stability is another quality of the products of this invention. Evidencing such stability is the fact that these products experience less than about 15% weight loss at 400° C. when subjected to thermogravimetric analysis. A preferred thermogravimetric weight loss profile is as follows:

|  | 200° C. | 300° C. | 400° C. |
| --- | --- | --- | --- |
| Percent Weight Loss | <0.1 | <0.5 | <10.0 |

The decabromodiphenylethane predominate products of this invention can be produce by a process which comprises: charging a reaction vessel with a catalytic amount of bromination catalyst and liquid elemental bromine ($Br_2$); feeding, through a small diameter dip tube, liquid diphenylethane to the reaction vessel at a point which is beneath the level of the charged liquid bromine, the liquid diphenylethane fed being in an amount which provides from about 0.0625 to about 0.033 moles of diphenylethane per mole of elemental bromine initially charged; maintaining the reaction mass at a temperature within the range of from about 30° C. to about 80° C. during the liquid diphenylethane feed; recovering an intermediate decabromodiphenylethane predominate product from the reactor; and fracturing, drying, and heat treating or drying, heat treating, and fracturing the intermediate product to yield the desired final decabromodiphenylethane product.

It is preferred that the bromine charged to the reactor be essentially anhydrous, i.e. less than 50 ppm water, and contain little, if any iron, and no more than 10 ppm, and preferably less than 5 ppm, organic impurities, e.g. oil, grease, and carbonyl containing hydrocarbons. With such a bromine purity, there is little, if any, impact on the color attributes of the decabromodiphenylethane product. Available, commercial grade bromine may have such a purity. If, however, such is not available, the organic impurities and water content of the bromine can be conveniently reduced by mixing together a 3 to 1 volume ratio of bromine and concentrated (94–98 percent) sulfuric acid. A two-phase mix is formed which is stirred for 10–16 hours. After stirring and settling, the sulfuric acid phase, along with the impurities and water, is separated from the bromine phase. To further enhance the purity of the bromine, the recovered bromine phase can be subjected to distillation.

The bromination catalyst used in the process is preferably $AlCl_3$ and/or $AlBr_3$, although use may be made of aluminum powder, iron powder, $FeCl_3$, $FeBr_3$, $ZrCl_4$, $ZrBr_4$ alone or in combination with the aluminum trihalide(s). Other bromination catalysts are suitable provided that they have sufficient catalytic activity to provide for the extent of bromination called for under the process conditions which will be encountered. Catalytic quantities are used. Typically, the catalysts will be present in an amount within the range of about 0.to about 20 weight percent, based on the weight of the diphenylethane reactant used in the process. A preferred amount is within the range of from about 6 to about 15 weight percent on the same basis, with from about 8.0 to about 11.0 weight percent being most preferred. Preferably, the amount of catalyst used is kept as low as possible without deleteriously affecting perbromination, for example, a catalyst to bromine ratio of 0.38–0.45 wt % is especially useful.

The bromination catalyst and bromine can be charged to the reaction vessel in any order or together. Care should be taken not to aspirate atmospheric moisture into the reaction vessel as the presence of moisture in the reaction vessel can cause a partial or total deactivation of the bromination catalysts.

The amount of elemental bromine ($Br_2$) charged to the reaction vessel should provide sufficient bromine to effect the degree of bromination sought and to provide an easily stirred reaction mass. Generally, the amount of $Br_2$ charged should provide a stoichiometric excess. It is preferred that the $Br_2$ amount charged be in excess of about 125% of the stoichiometric amount. The most preferred amount of $Br_2$ charged is from about 150% to about 175% of stoichiometric. After the reaction is complete, the bromine not used in the reaction will be a liquid component of the reaction mass and will continue to serve the before-mentioned purpose of facilitating the formation and the maintenance of a stirrable reaction mass.

The diphenylethane can be commercially obtained or can be produced by various routes. For example, CA 97 3865d (Japanese Kokai 82/45114) and CA 46 7084g disclose the reaction of benzene and ethylene dihalide in the presence of aluminum trichloride to yield diphenylethane. Another process for producing diphenylalkane includes the oxidative dimerization of toluene at a temperature of at least 400° C. in the presence of a metal oxide catalyst to yield diphenylethane and diphenylalkene. The latter product is then hydrogenated to remove the olefinic unsaturation.

It is not uncommon for the diphenylethane reactant to be accompanied by various impurities which may be detrimental to the color of the final product. Exemplary of such impurities are diphenylmethane, stilbene, benzene, alkylated diphenylethane and diphenylmethane, and tetrahydronaphthalene. If the amounts of the impurities becomes troublesome, then they can usually be reduced by conventional techniques, for example, the diphenylethane can be purified by recrystallization. For best results, a purity of 99.9% is preferred. See Example III wherein a recrystallization method is described.

The diphenylethane is fed to the reaction vessel in the molten state and thus at a temperature above its melting point but not at a temperature which is so high that the diphenylethane experiences degradation. For diphenylethane, the melting point is about 53° C. to 55° C. and, hence, diphenylethane is preferably fed at a temperature within the range of from about 55° C. to about 80° C. The higher temperatures are preferred as the viscosity of the molten diphenylethane is lower thus making its feed to the reaction vessel more convenient. Most preferred is a temperature within the range of from about 70° C. to about 80° C.

It is preferred that the molten diphenylethane be blanketed by a non-oxidizing atmosphere until it is fed into the reaction vessel. Such an atmosphere can be provided by most inert gases. For example, nitrogen, argon, neon, helium, krypton, xenon, and the like. By providing the inert atmosphere, it has been found that there is a prevention or at least a reduction in the production of oxidation decomposition impurities in the diphenylethane feed. The decomposition impurities are probably 1-hydroxy-1,2-diphenylethane, benzaldehyde, benzyl alcohols and the like. The significant presence of these impurities, can adversely affect the final color of the final product of this invention.

The addition of the diphenylethane below the liquid level of the bromine in the reaction vessel is an important feature of the process. It has been found that with this sub-surface feed, a reaction product having a high average bromine number is obtained more quickly than is the case when the liquid diphenylethane is fed above the liquid surface of the bromine. The depth below the liquid bromine surface at which the feed is to occur is that depth which is sufficient to diminish or obviate splattering of the reaction mass as the feed is occurring. Generally, a depth of from about 0.5 inches (1.27 cm) to about 1.0 inches (2.54 cm), for laboratory scale equipment, and from about 6 inches (15.24 cm) to about 6 feet (183 cm), for commercial scale equipment is suitable. In almost all cases, a depth of about one-half inch (1.27 cm) will be functional.

As mentioned above, the diphenylethane is fed to the reactor through a small diameter dip tube. The use of the small diameter dip tube and a high velocity feed rate has an apparent favorable impact on the final color of the products of this invention. While not desiring to be bound by theory it is believed that the high velocity feed rate achieved with the small diameter dip tube provides a jet stream of diphenylethane, which on a microscopic scale entrains sufficient bromine in the jet stream to perbrominate adjacent diphenylethane molecules. As the diameter of the dip tube is decreased, the time required to entrain sufficient bromine is decreased, i.e. micro-mixing of diphenylethane and bromine is increased. This micro-mixing effect is best illustrated in FIG. 1 with temperature-time curves having peak temperatures of about 260° C. (Points 2, 4, and 6). At the peak temperature, a microscopic droplet of diphenylethane has theoretically mixed and reacted with 10 moles of bromine per mole of diphenylethane. Since the reaction takes place in excess bromine, there is a cooling effect over time as the perbrominated species are further mixed with bromine. Curve A in FIG. 1 represents a dip tube size of 4.76 mm wherein the diphenyl ethane feed rate is about 447 centimeters per second. Curve B utilizes a 12.7 mm dip tube and a flow rate of about 63 centimeters per second, and Curve C has a flow rate of about 15.7 centimeters per second and a dip tube size of 24.4 mm. By maximizing the reaction rate (minimizing the time) for perbrominating diphenylethane, it is believed that the amount of color causing side reactions is minimized. As the reaction rate decreases, i.e. the time for perbromination increases, and the amount of color causing impurities also increases. The same effect of maximizing the reaction rate by increasing the micro-mixing has been demonstrated on a small scale by increasing the agitation rate in the reaction vessel.

In addition to providing a product with enhanced color characteristics, the decrease in color causing impurities also results in an increase in the particle size of the decabromodiphenylethane thus produced. Preferably, the particle size is greater than 10 microns, more preferably, greater than 12 microns, and most preferably greater than about 15 microns.

For a commercial plant, agitation rates of 20 to 150 revolutions per minute (rpm) and dip tubes having an inside tube diameter of from about 4.76 mm to about 15.87 mm are useful for providing sufficient micro-mixing. A particularly, useful dip tube is one in which the inside diameter is either 4.76 mm or 12.7 mm. In some cases it may be desirable to use multiple dip tubes so that the overall diphenylethane feed rate to the reaction vessel is kept at a level which gives good process efficiency. In selecting a diphenylethane feed rate, consideration should also be given for the need to control the reaction temperature and the hydrogen bromide evolution. Preferred diphenylethane feed rates are in the range of from about 50 to 800 centimeters per second, more preferably from about 200 to about 700 centimeters per second, and most preferably from about 250 to about 600 meters per second.

For small scale reactions, agitation rates in the range of from about 90 to about 130 rpm, and dip tubes having an inside diameter of from about 0.5 mm to about 1.25 mm are suitable. A preferred dip tube inside diameter is about 0.75 mm.

Generally, the total amount of diphenylethane fed to the reaction vessel will provide from about 0.0625 to about 0.033 moles of diphenylethane per mole of bromine initially charged. Preferably, from about 0.055 to about 0.035 moles of diphenylethane will be fed per mole of bromine initially charged. The most preferred ratio is in the range of from about 0.043 to about 0.037 moles of diphenylethane per mole of bromine.

During the diphenylethane feed, the reaction mass temperature is kept within the range of from about 30° C. to about 80° C., and preferably within the range of from 50° C. to about 60° C. Since the bromination of diphenylethane is exothermic, cooling of the reaction mass may be needed to obtain the addition temperature chosen. The heat of reaction can be removed from the reaction mass by cooling the reaction vessel or by having the reaction mass under reflux conditions so that heat can be removed by the use of an overhead condenser. During the diphenylethane feed, the temperature of the reaction mass is preferably at least 45° C. and most preferably above the melting point of the diphenylethane. Lower temperatures can be used, however, the diphenylethane feed velocity must be sufficiently high to prevent freeze-up of the molten feed in the dip tube which is in contact with the relatively cool reaction mass.

The process can be run so that the pressure in the reaction vessel provides a refluxing condition at the selected reaction mass temperature. With a refluxing condition, control of the reaction mass temperature is facilitated. If temperature control is effected otherwise, i.e. by the use of heating or cooling jackets, etc. then the pressure can be any which is not prohibitive of the obtainment of the various defined parameters of the process. Also since temperatures above the boiling point of bromine are useful in the process, super atmospheric pressures, e.g. 5 psig can be used to obtain same.

After the diphenylethane feed is partially complete, the overhead can be blocked to allow the reaction vessel pressure to build as more and more HBr is produced. Once the diphenylethane feed is completed, the reaction mass is then discharged from the reaction vessel by the simple expedient of using the built-up pressure in the reaction vessel. Generally, no significant post diphenylethane feed cook period is required, and the discharge can occur as soon as is practical after the bromination reaction ceases.

Since the bromination reaction is a substitution reaction, HBr will be evolved so long as bromination is occurring. Hence, the evolution of HBr from the reaction mass can be used as an indicator to determine when a substantially perbrominated reaction product has been obtained. The practitioner need only monitor the reaction for the cessation of HBr production and its evolution from the reaction mass.

After the reaction has at least substantially ceased, the reaction mass will comprise a liquid-solid mixture. The solid comprises brominated diphenylethane, entrained bromine and other impurities. The liquid will comprise mostly bromine. The recovery of the brominated diphenylethane product and its entrained bromine can be effected conventionally by steam stripping of the reaction mass to remove non-entrained bromine. Other separation techniques can be used, e.g. filtration, but steam stripping is preferred as not only does it separate the liquid, i.e. the remaining non-entrained bromine, from the solids, but also the steam acts to deactivate the catalyst. The introduction of the steam preferably occurs after the bromination activity has ceased. Another apparent advantage of the products of this invention is seen during the steam strip, i.e. the solid product produced does not tend to aggregate during the stripping step.

After the steam strip, the remaining solids, which are predominate in decabromodiphenylethane, can be first washed with an aqueous base, e.g. an aqueous solution of NaOH or $Na_2CO_3$, to neutralize and remove HBr and free $Br_2$ present. After this caustic wash, the product is water-washed.

The washed product is further treated to remove entrained free bromine therefrom. Such bromine is deleterious to color and to product quality and its removal can be effected by heat-treating the product at a temperature within the range of from about 200° C. to about 250° C. for 6 to 20 hours and then fracturing the hot product particles by grinding, milling etc. Interestingly, it has been observed that enhanced color is obtained if the fracturing of the product precedes the heat-treating step.

The decabromodiphenylethane predominant product of this invention may be used as a flame retardant in formulation with virtually any flammable material. The material may be macromolecular, for example, a cellulosic material or a polymer. Illustrative polymers are: olefin polymers, cross-linked and otherwise, for example, homopolymers of ethylene, propylene, and butylene; copolymers of two or more of such alkylene monomers and copolymers of one or more of such alkylene monomers and any other copolymerizable monomers, for example, ethylene/propylene copolymers, ethylene/ethyl acrylate copolymers and ethylene/vinyl acetate copolymers; polymers of olefinically unsaturated monomers, for example, polystyrene, e.g. high impact polystyrene, and styrene copolymers; polyurethanes; polyamides; polyimides; polycarbonates; polyethers; acrylic resins; polyesters, especially poly(ethyleneterephthalate) and poly(butyleneterephthalate); epoxy resins; alkyls; phenolics; elastomers, for example, butadiene/styrene copolymers and butadiene/acrylonitrile copolymers; terpolymers of acrylonitrile, butadiene and styrene; natural rubber; butyl rubber; and polysiloxanes. The polymer may also be a blend of various polymers. Further, the polymer may be, where appropriate, cross-linked by chemical means or by irradiation.

The amount of product used in a formulation will be that quantity needed to obtain the flame retardancy sought. It will be apparent to the practitioner that for all cases no single precise value for the proportion of the product in the formulation can be given since this proportion will vary with the particular flammable material, the presence of other additives and the degree of flame retardancy sought in any given application. Further, the proportion necessary to achieve a given flame retardancy in a particular formulation will depend upon the shape of the article into which the formulation is to be made, for example, electrical insulation, tubing and film will each behave differently. In general, however, the formulation may contain from about 5 to about 40 wt. percent, preferably 10 to 30 weight percent, of the product when it is the only flame retardant compound in the formulation.

It is especially advantageous to use the product with an inorganic compound, especially ferric oxide, zinc oxide, zinc borate, the oxide of a Group V element, for example, bismuth, arsenic, phosphorus and especially antimony, in the formulation. Of these compounds, antimony oxide is especially preferred. If such a compound is present in the formulation, the quantity of product needed to achieve a given flame-retardancy is accordingly reduced. Generally, the product and the inorganic compound are in a weight ratio of from about 1:1 to about 7:1, and preferably of from about 2:1 to about 4:1.

Formulations containing a flame retardant system comprised of the product of this invention and the above inorganic compounds may contain up to about 40 percent by weight of the system and preferably between 20 percent and 30 percent by weight.

Any of the additives usually present in formulations, e.g. plasticizers, antioxidents, fillers, pigments, UV stabilizers, etc. can be used in formulation with the product of this invention.

Thermoplastic articles formed from formulations containing a thermoplastic polymer and a product of this invention can be produced conventionally, e.g. by injection molding, extrusion molding, compression molding, and the like.

The Y.I. values used herein were obtained in accordance with ASTM D 1925 and with a Hunter Lab Model Colorquest 45°/0°. Y.I. values are calculated values, i.e. $Y.I. = 100(0.72a + 1.79b)/L$, wherein the values for "a", "b", and "L" are observed values The "a" value measures redness when a plus value, gray when zero and greenness when a negative value. The "b" value measures yellowness when a plus value, gray when zero and blueness when a minus value. The "L" value measures lightness and varies from 100, for perfect white, to 0, for black. The "L" value is used by some in the industry to convey a sense of the degree of whiteness of a material. In that respect, the product of this invention preferably will yield an "L" value within the range of from about 90 to about 95.

Examples I–IV describe processes for the preparation of decabromodiphenylethane predominate products of this invention on a small scale. Examples V and VI describe processes which are substantially identical to the processes of Examples I–IV but which do not produce decabromodiphenylethane predominate products having the "whiteness" of the products of Examples I–IV.

EXAMPLE I

A 500 mL round-bottom flask was equipped with a mechanical stirrer, a thermometer, an addition funnel heated with a heat gun and a dip tube extending therefrom, a heating mantle and a reflux condenser vented to a water scrubber in line with a dry ice condenser. The dip tube had a nominal inside diameter of 0.75 mm. The addition funnel was charged with ground diphenylethane (36.4 grams, 0.2 moles), and heated slowly with the heat gun. The flask was charged with 258 mL bromine, and catalyst ($AlCl_3$, 3.6 grams). The diphenylethane was obtained from Hardwicke and had a purity of 99.9%. Its water content was 356 ppm. The level of the liquid bromine in the flask covered the end of the dip tube by about 19 mm. Molten diphenylethane (kept at 55°–66° C.) was then added, through the dip tube, beneath the surface of the bromine over a period of about 92 minutes. During the addition, the flask temperature was kept at 55° C. and the flask was agitated with the stirrer being run at 120 rpm. After the addition was complete, the reaction mixture was refluxed at 60° C. for 0.7 hour, and then allowed to cool to 40° C. over about a 30 minute period. Water was added (125 mL) and the reaction mass was steam distilled until a vaporhead temperature of 97° C. was obtained. To the remaining mass was added 60 mL of water and 60 mL of a 25 percent aqueous NaOH solution. The resultant slurry was centrifuged and the recovered solids were washed with deionized water until neutral. The washed solids were oven dried at 100° C. for one hour. The dried product was then jet milled in a Micron Master Jet Pulverizer Model 02-506, manufactured by Jet Pulverizer Co. of Palmyra, N.J., to obtain an average particle size of 2.5 to 3.5 microns. The milled product was then heat-treated for 6 hours at 230° C.

EXAMPLE II

The procedure of Example I was repeated except that the dried product was heat-treated and then jet milled.

EXAMPLE III

The procedure of Example I was repeated except that the diphenylethane was fed in 77 minutes.

EXAMPLE IV

The procedure of Example I was repeated except that the diphenylethane was fed in 95 minutes.

EXAMPLE V

The procedure of Example IV was repeated except that the dried product was heat-treated and then jet milled.

EXAMPLES VI AND VII

The procedure of Example I was repeated twice except for the use of a dip tube having a nominal inside diameter of 4.75 mm and except for the use of the following minor process variations: the diphenylethane addition was over 94 minutes; the bromine had been pretreated by being stirred over $H_2SO_4$ for about 6 hours; the reaction mixture was refluxed for 1 hour; the amount of water added to the reaction mass was 300 mL; steam distillation was ceased when the overhead temperature reached 100° C.; after steam distillation, the remaining reaction mass was treated with 25 mL of a 50% aqueous NaOH solution; the water washed solids were air dried overnight; and the dried product was heat-treated and then jet milled.

EXAMPLE VIII

The procedure of Examples VI and VII was repeated except that the diphenylethane was dried before being fed to the vessel under nitrogen at a temperature of 75°-80° C. for a period of 4 hours.

The following Table 1 reports on the colorimetric values for the various products produced in Examples I-VIII.

TABLE 1

| Example | Dip Tube Inside Diameter* | Feed Rate (cm/sec) | Post Treatment | Hunter Values a, b, L | Y.I. |
|---|---|---|---|---|---|
| I | 0.75 mm | 1.68 | Jet Milled then Oven-Aged | a = −0.16 b = 4.11 L = 93.5 | 7.7 |
| II | 0.75 mm | 1.68 | Oven-Aged then Jet Milled | a = −0.10 b = 3.55 L = 90.6 | 6.9 |
| III | 0.75 mm | 2.00 | Jet Milled then Oven-Aged | a = −0.19 b = 3.68 L = 94.2 | 6.8 |
| IV | 0.75 mm | 1.63 | Jet Milled then Oven-Aged | a = −0.23 b = 4.39 L = 94.2 | 8.1 |
| V | 0.75 mm | 1.63 | Oven-Aged then Jet Milled | a = −0.24 b = 3.73 L = 89.9 | 7.2 |
| VI | 4.75 mm | 0.04 | Oven-Aged then Jet Milled | a = −0.26 b = 6.25 L = 88.2 | 12.4 |
| VII | 4.75 mm | 0.04 | Oven-Aged then Jet Milled | a = −0.26 b = 6.11 L = 87.8 | 12.3 |
| VIII | 4.75 mm | 0.04 | Oven-Aged then Jet Milled | a = −0.30 b = 5.62 L = 88.21 | 11.1 |

The following Example illustrates a commercial scale production of decabromodiphenylethane wherein the agitator speed is varied between 80 and 120 RPM.

EXAMPLE IX

Diphenylethane (799 to 901 kilograms) is fed to a 15,000 liter glass-lines reactor having one vertical baffle and containing 100 to 150% stoichiometric excess bromine. The vessel contains an agitator and an overhead condenser. The feed rate of the diphenylethane ranges from 5.5 and 8.5 centimeters per second, and the amount of catalyst is varied between 0.3 and 0.6 weight percent based on the weight of diphenylethane. The reaction (runs 1-13) is conducted at a temperature of 57° C. Run 14 is conducted at 68° C. The product from each run is heat treated at about 230° C. for about 6 hours after drying and grinding the particles to an average of about 7 microns. Reaction conditions and product made generally in accordance with the foregoing procedure are given in the following Table 2.

TABLE 2

| Run | Dip Tube Inside Diameter* | Feed Rate (cm/sec) | Agitator RPM | Particle Size** (microns) | Y.I. (ASTM D 1925) |
|---|---|---|---|---|---|
| 1 | 25.4 mm | 6.8 | 120 | 14.9 | 15.8 |
| 2 | 25.4 mm | 6.6 | 120 | 14.0 | 12.9 |
| 3 | 25.4 mm | 7.1 | 120 | 17.1 | 13.3 |
| 4 | 25.4 mm | 5.3 | 120 | 11.9 | 13.5 |
| 5 | 25.4 mm | 6.6 | 100 | 20.4 | 12.3 |
| 6 | 25.4 mm | 8.6 | 80 | 26.0 | 13.2 |
| 7 | 25.4 mm | 8.6 | 80 | 21.7 | 13.6 |
| 8 | 25.4 mm | 8.8 | 80 | — | 11.8 |
| 9 | 25.4 mm | 7.9 | 80 | 12.9 | 13.6 |
| 10 | 25.4 mm | 7.6 | 80 | 25.4 | 13.6 |
| 11 | 25.4 mm | 7.9 | 80 | 20.3 | 14.6 |
| 12 | 25.4 mm | 7.6 | 80 | — | — |
| 13 | 25.4 mm | 7.4 | 80 | 24.4 | 15.1 |
| 14 | 25.4 mm | 7.8 | 80 | 13.4 | 14.7 |

*The dip tube inside diameters are approximate diameters.
**Particle size determined on centrifuge cake before grinding.

The foregoing Runs 1-14 illustrate the effect that changing the agitator RPM has on the Y.I. value of the decabromodiphenylethane product for low velocity feed rates.

EXAMPLE X

In the next series of runs (15-31), dip tubes of 4.76 mm to 12.7 mm are used and the feed rates are varied between 0.56 and 540 centimeters per second. Agitator speeds of from 20 to 80 RPM are used. Diphenylethane (571 to 1239 kilograms) is fed to the 15,000 liter glass-lines reactor of Example IX containing 130 to 230% stoichiometric excess bromine. The amount of catalyst is varied between 0.3 and 0.5 weight percent based on the weight of diphenylethane. The reaction is conducted at a temperature of 57° C. All of the products are heat treated at about 230° C. for about 6 hours after drying and grinding the particles to an average of about 7 microns. Reaction conditions and product made generally in accordance with the foregoing procedure are given in the following Table 3.

TABLE 3

| Run | Dip Tube Inside Diameter* | Feed Rate (cm/sec) | Agitator RPM | Particle Size** (microns) | Y.I. (ASTM D 1925) |
|---|---|---|---|---|---|
| 15 | 12.7 mm | 64 | 80 | 27.2 | 10.7 |
| 16 | 12.7 mm | 61 | 50 | 34.1 | 10.7 |
| 17 | 12.7 mm | 66 | 50 | 32.0 | — |
| 18 | 4.76 mm | 422 | 50 | 26.2 | 10.9 |
| 19 | 4.76 mm | 280 | 50 | 35.3 | 13.5 |
| 20 | 4.76 mm | 542 | 50 | 23.3 | 12.8 |
| 21 | 12.7 mm | 71 | 50 | 37.7 | 13.2 |
| 22 | 12.7 mm | 56 | 20 | 28.2 | 17.3 |
| 23 | 12.7 mm | 60 | 20 | 16.4 | 14.6 |
| 24 | 4.76 mm | 265 | 20 | 64.2 | 12.8 |
| 25 | 4.76 mm | 296 | 20 | 19.9 | 12.2 |
| 26 | 4.76 mm | 332 | 60 | 73.1 | 12.7 |
| 27 | 4.76 mm | 345 | 60 | 50.7 | 12.1 |
| 28 | 4.76 mm | 335 | 60 | 22.4 | 10.9 |
| 29 | 4.76 mm | 423 | 60 | — | 11.3 |
| 30 | 4.76 mm | 296 | 60 | — | 12.2 |

*The dip tube inside diameters are approximate diameters.
**Particle size determined on centrifuge cake before grinding.

From the foregoing Tables 1, 2 and 3 it is seen that products of this invention can obtain a Y.I. value of less than 11 by the use of a dip tube having a suitably small inside diameter and/or by varying the agitation speed in order to obtain micro-mixing of the diphenylethane, bromine, and catalyst. While the larger scale runs do not achieve the same level of micro-mixing as can be obtained in the small scale runs, there is an improvement in Y.I. values as the feed rate of diphenylethane is increased.

The following example illustrates a method for purifying diphenylethane.

EXAMPLE XI

A 1-L beaker was charged with methanol (300 mL). Crude diphenylethane (300 grams) was then added. The contents of the beaker were heated and stirred at 65° C., and the resulting clear solution was then allowed to cool slowly to room temperature. A crystalline solid was formed. The solid was filtered and washed once with 120 mL methanol and then dried. The recovery was 274.5 grams (91.5%). The recrystallized material had a melting point of 50° C.-54° C. which is slightly higher than the 49° C.-50° C. for the original starting diphenylethane. The starting diphenylethane had a Y.I. of 33.2 (L=81.2, a=−2.9, b=16.1) while the recrystallized diphenylethane material had a Y.I. of 2.8 (L=90.8, a=−0.4, b=1.4).

Variations of the invention are within the spirit and scope of the appended claims.

What is claimed is:

1. An improvement in a process for preparing a product predominant in decabromodiphenylethane, wherein the diphenylethane is reacted with bromine in the presence of bromination catalyst by feeding diphenylethane to a reaction vessel below the liquid level of bromine in the reaction vessel, the improvement comprising contacting diphenylethane, bromine, and a catalyst at a rate sufficient to obtain a diphenylethane predominant product having a yellowness index (Y.I.) (ASTM D-1925), after heat treating, between about 5 and about 11 and a particle size before grinding of greater than about 15 microns up to about 73 microns, wherein the contacting is effected by feeding diphenylethane to the reaction vessel through one or more dip tubes each having an inside tube diameter of from about 4.76 mm to about 15.87 mm such that the feed rate is in the range of from about 50 to about 800 centimeters per second for a commercial scale plant, and wherein the total amount of diphenylethane fed ranges from about 0.033 to about 0.0625 moles of diphenylethane per mole of bromine.

2. The process of claim 1 wherein the diphenylethane is 1,2-diphenylethane.

3. The process of claim 1 wherein the bromination of diphenylethane is effected at a temperature within the range of from about 30° C. to about 80° C.

4. A process for preparing a product predominant in decabromo-1,2-diphenylethane by reacting 1,2-diphenylethane with bromine in the presence of a catalytic amount of bromination catalyst in a reaction vessel, the process comprising: (a) feeding from about 0.033 to about 0.0625 moles of diphenylethane per mole of bromine to the reaction vessel, below the liquid level of bromine in the reaction vessel through one or more dip tubes each having an inside tube diameter of from about 4.76 mm to about 15.87 mm at a rate in the range of from about 50 to about 600 centimeters per second, (b) maintaining said 1,2-diphenylethane, bromine, and catalyst at a temperature in the range of from about 30° to about 80° C. during said feeding and reaction; (c) recovering said product predominant in decabromo-1,2-diphenylethane which product has an average particle size before grinding of greater than about 15 microns up to about 73 microns; and (d) heat treating the product at a temperature and for a period of time sufficient to obtain a product having a yellowness index (Y.I.) (ASTM D-1925), after heat treating, between about 5 and about 11.

5. The process of claim 4 wherein the reaction temperature is in the range of from about 50° C. to about 60° C.

6. A process for preparing a product predominant in decabromodiphenylethane having a yellowness index (Y.I.) value within the range of from about 5 to 11 as measured by ASTM D 1925, and a particle size of greater than about 15 microns up to about 73 microns, the process comprising (a) feeding an amount of diphenylethane to a reaction vessel containing bromine and a bromination catalyst; (b) maintaining, during said feeding, a reaction time-temperature profile whereby the rate of reaction between the diphenylethane and bromine is maximized so as to minimize color causing side reactions; (c) separating the decabromodiphenylethane predominant product from the bromine and catalyst; and (d) heat treating the product at a temperature and for a period of time sufficient to obtain a product having a yellowness index (Y.I.) value between about 5 and about 11 as measured by ASTM D 1925, wherein the amount of diphenylethane fed to the reaction vessel is in the range of from about 0.037 to about 0.043 moles of diphenylethane per mole of bromine.

* * * * *